United States Patent [19]

Tsutsumi et al.

[11] 4,309,447
[45] Jan. 5, 1982

[54] SKIN-PROTECTING COSMETIC COMPOSITION

[75] Inventors: Hisao Tsutsumi, Miyashiro; Yoshiaki Abe, Tokyo; Shigeo Inoue, Ichikai; Atsuo Ishida, Chiba, all of Japan

[73] Assignee: Kao Soap Co., Ltd., Tokyo, Japan

[21] Appl. No.: 73,135

[22] Filed: Sep. 6, 1979

[30] Foreign Application Priority Data

Sep. 29, 1978 [JP] Japan .................. 53-120272

[51] Int. Cl.³ .............................. A61K 7/48
[52] U.S. Cl. ................. 424/361; 424/61; 424/70; 424/168; 424/358
[58] Field of Search ............ 424/361; 536/119, 120

[56] References Cited

U.S. PATENT DOCUMENTS 4,195,177  3/1980  Inoue et al. .................. 424/361

FOREIGN PATENT DOCUMENTS 2371921  6/1978  France ................. 424/361
682717   2/1965  Italy .................... 424/361
37-37448 6/1962  Japan ................... 424/361
50-47541 5/1975  Japan ................... 424/361

*Primary Examiner*—Dale R. Ore
*Attorney, Agent, or Firm*—Oblon, Fisher, Spivak, McClelland & Maier

[57] ABSTRACT

A skin-protecting cosmetic composition comprising a hydroxypropyl-etherified glycolipid ester represented

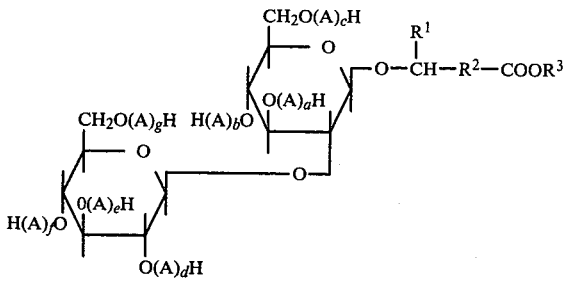

wherein $R^1$ represents a methyl group or a hydrogen atom; $R^2$ represents a saturated or unsaturated hydrocarbon group having carbon atoms of 11 to 15 when $R^1$ is a methyl group, or a saturated or unsaturated hydrocarbon group having carbon atoms of 12 to 16 when $R^1$ is a hydrogen atom; a represents the group

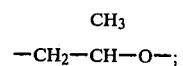

$R^3$ represents a saturated or unsaturated hydrocarbon group having carbon atoms of 1 to 20 or $-(A)_hH$; and a, b, c, d, e, f, g and h are each integers, whose sum ranges from 1 to 60.

3 Claims, No Drawings

SKIN-PROTECTING COSMETIC COMPOSITION

BACKGROUND OF THE INVENTION

1. Field of the Invention

This invention relates to cosmetics for use in skin protection, more particularly to a skin-protecting cosmetic composition containing a hydroxypropyl-etherified glycolipid ester (hereinafter abbreviated as "POSL") represented by the formula (I),

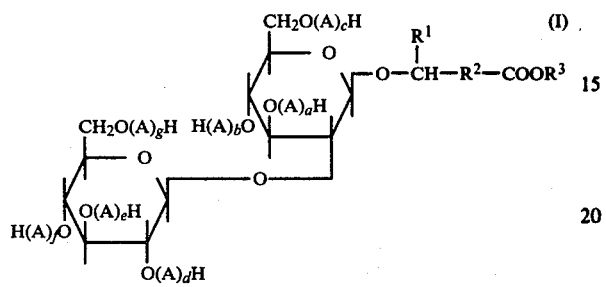

wherein $R^1$ represents a methyl group or a hydrogen atom; $R^2$ represents a saturated or unsaturated hydrocarbon group having carbon atoms of 11 to 15 when $R^1$ is a methyl group, or a saturated or unsaturated hydrocarbon group having carbon atoms of 12 to 16 when $R^1$ is a hydrogen atom; A represents the group

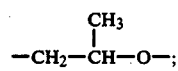

$R^3$ represents a saturated or unsaturated hydrocarbon group having carbon atoms of 1 to 20 or $-(A)_hH$; and a, b, c, d, e, f, g and h are eachintegers, whose sum ranges from 1 to 60.

2. Description of the Prior Art

Skin-protecting cosmetics have been used to prevent the skin from chapping and keep the same fresh-looking. For this purpose, there have been proposed hand creams, cold creams, vanishing creams, milky lotions, beauty washes and the like. These skin-protecting cosmetics are, in general, in the form of an emulsion or solution by emulsification or solubilization of various oil substances with surface active agents. Such oil substances include, for instance, hydrocarbons such as liquid paraffin, vaseline, paraffin wax, squalane, ceresine wax and the like; esters such as bees wax, spermaceti, carnauba wax, lanolin and synthetic esters of higher alcohols and fatty acids; alcohols such as long-chain aliphatic alcohols, lanolin alcohol and the like; and fatty acids.

The skin-protecting cosmetics are intended primarily to function such that the oil membrane formed on the skin after the evaporation of the moisture from inside of the skin acts as a barrier against the stimuli from outside and prevents the moisture in the skin from drying and hence protects the skin. However, the oil substance often causes damage to the skin because the oil itself is degenerated, for example, by oxidation when the oil membrane remains on the skin over a long period of time.

Therefore, the oil substance should possess a barrier ability against the stimuli from outside, that is, a blocking property, and at the same time, should be removed easily by washing. The usual oil substances known in the art have an excellent barrier ability but are liable to remain deposited on the skin even after washing, thereby resulting in damaged skin.

The present inventors have examined a wide variety of oil substances capable of protecting the skin and being easily removed by washing. As a result, they have found that POSL of the formula (I) achieves the above desired properties and that the oil substances present in the known skin-protecting cosmetics may be wholly or partially replaced by POSL.

Based on this finding, the present invention has been accomplished.

SUMMARY OF THE INVENTION

The present invention provides a skin-protecting cosmetic composition which comprises POSL represented by the formula (I) and which imparts satisfactory protection and freshness to the skin, coupled with easy removal by washing with water.

DETAILED DESCRIPTION OF THE PREFERRED EMBODIMENTS

POSL to be used in the invention is a novel compound which can be produced, for instance, by reacting glycolipid or a glycolipid ester represented by the formula (II),

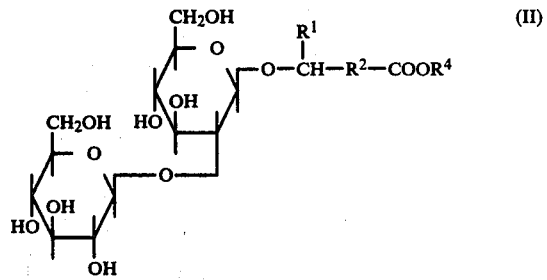

wherein $R^4$ represents a saturated or unsaturated hydrocarbon group having carbon atoms of 1 to 20 or a hydrogen atom, with propylene oxide in the presence of an alkali catalyst (see U.S. Patent application Ser. No. 962,664) filed Nov. 21, 1978.

The total number of carbon atoms of $R^1$ and $R^2$ in POSL is preferably 12 to 16, and the addition mole number of propylene oxide (the sum of a to h) is preferably 1 to 60. Beyond the limits, POSL markedly lowers in the cleansing ability and loses its function as an oil substance.

Particularly preferred POSL has hydrocarbon groups of 14 to 16 carbon atoms of $R^1$ and $R^2$ in their total number, and propylene oxide of 5 to 20 in its addition mole number.

The properties of POSL which is useful in and typical of the invention are shown below.

| $R^1$ | $R^2$ | $R^3$ | Addition mole number | Hydroxy value | Acid value | Saponification value | Appearance |
|---|---|---|---|---|---|---|---|
| $CH_3$ | $C_{15}H_{28}$ | $CH_3$ | 5 | 420.3 | 0.2 | 61.3 | |

-continued

| R¹ | R² | R³ | Addition mole number | Hydroxy value | Acid value | Saponification value | Appearance |
|---|---|---|---|---|---|---|---|
| | | | 7 | 376.5 | 0.7 | 53.5 | Viscous paste substance |
| | | | 15 | 261.5 | 0.3 | 37.0 | |
| | | | 30 | 167.2 | 1.2 | 21.5 | |
| $CH_3$ | $C_{15}H_{28}$ | $C_{12}H_{25}$ | 7 | 325.3 | 0.2 | 47.0 | Paste-like wax substance |
| | | | 15 | 236.2 | 0.8 | 31.5 | |
| | | | 30 | 159.3 | 0.5 | 20.7 | |
| $CH_3$ | $C_{15}H_{28}$ | $-(A)_hH$ | 5 | 492.0 | 0.7 | 60.5 | Viscous paste substance |
| | | | 8 | 413.5 | 0.0 | 51.5 | |
| | | | 15 | 299.0 | 0.1 | 37.5 | |
| | | | 30 | 185.3 | 0.0 | 23.8 | |

In general, POSL itself is only slightly soluble in water and has oily characteristics but may be obtained in the form of an emulsion by emulsification with a surface active agent which exhibits an excellent application feeling and allows for easy removal by washing with water.

The skin-protecting cosmetic composition according to the present invention can be produced in the same manner as in the conventional cosmetics, except that the whole or part of the oil substances contained in the cosmetics is replaced by POSL, preferably in amounts of 0.1 to 100 percent by weight. Where it becomes suitable, other additives or components known in the art can be advantageously utilized which include various oil substances, surface active agents, alcohols, viscosity modulators, antiseptics, drugs, pigments, perfumes, wetting agents and water.

Examples of oil substances are described hereinbefore. Examples of surface active agents are polyoxyethylene alkyl ether, polyoxyethylene fatty acid ester, polyoxyethylene sorbitan fatty acid ester, sorbitan fatty acid ester, glycerine fatty acid ester, polyoxyethylene glycerine fatty acid ester, polyoxyethylene hardened castor oil, polyoxyethylene sorbitol fatty acid ester, polyoxyethylene polyoxypropylene condensed products and the like. Examples of alcohols are ethanol, isopropanol and the like. Examples of viscosity modulators are carboxymethyl cellulose, methyl cellulose, hydroxyethyl cellulose, polyvinyl alcohol, polyvinyl pyrrolidone, tragacanth gum, carrageenan, locust been gum, dextrin, dextrin fatty acid ester, carboxyvinyl polymer, gelatin, sodium alginate, acacia and the like. Examples of wetting agents are sorbitol, glycerine, propylene glycol, 1,3-butylene glycol, pyrrolidone carbonic acid sodium salt, lactic acid, sodium lactate, polyethylene glycol and the like. Examples of antiseptics are p-hydroxybenzoic acid alkyl ester, sodium benzoate, potassium sorbate, phenoxyethanol and the like. Moreover, examples of drugs are vitamines, antiinflammatory agents and germicides.

By the term skin-protecting composition used herein are meant all cosmetic materials for purposes of skin protection which include, for instance, hand creams, cleansing creams, milky lotions, cold creams, vanishing creams, hair creams, foundation creams, beauty washes, facial packs and the like.

This invention will now be described with reference to certain specific Examples, but the invention is not limited to these Examples. The following Reference Example is illustrative of the preparation of POSL.

Reference Example (i) To a mixture of 1500 g of glucose, 75 g of a yeast extract and 15 g of urea was added water in an amount sufficient to adjust the whole volume to 15 l, and the resulting mixture was sterilized and used as a fermentation liquid. To this fermentation liquid was inoculated *Torulopsis bombicola* which had been cultured at 30° C. for 48 hours in a culture medium comprising the same composition as the fermentation liquid. The fermentation was initiated under the following conditions: temperature, 20° C.; stirring, 300 rpm; and aeration, 0.33 VVM. The fermentation was conducted for 24 hours after the inoculation of the microorganisms, and beef tallow was added in an amount of 150 g and then added in the same amount at intervals of 24 hours. The added beef tallow amounted to 900 g. After the final addition, the fermentation was carried out for further 24 hours. The fermentation time amounted to 168 hours. After the completion of the fermentation, the sophorolipid layer which had precipitated at the bottom of a fermentor was collected by decantation and filtration to give 1300 g of sophorolipid in the form of a paste containing about 50% of water.

(ii) 100 g of the thus obtained sophorolipid was placed in a 200 ml round bottom flask equipped with a stirrer and a Liebig condenser, together with 2.5 g of polypropylene glycol having an average molecular weight of 200. Water was removed by distillation on an oil bath (80° C.) with stirring under a reduced pressure of 250 mmHg. The distillation of water was completed in about 2 hours, and the water content at that time was found to be less 1%.

(iii) To the thus prepared polypropylene solution of sophorolipid were added 150 g of methanol and then 2.5 g of sulfuric acid. The mixture was reacted at 40°±2° C. for 90 minutes. The reaction was regarded as having been completed when many spots shown by the raw material or sophorolipid converged on one spot corresponding to a glycolipid methyl ester by thin-layer chromatography on silica gel [developing solvent: chloroform-methanol-acetic acid (75:20:5) ].

After the completion of the reaction, the mixture was made neutral with a given amount of potassium hydroxide and filtered with filtering paper. The filtrate was placed again in a round bottom flask equipped with a Liebig condenser, and methanol and methyl acetate were removed by distillation to obtain 48 g of a mixture containing 94% of a [(2'-O-β-D-glucopyranosyl-β-D-glucopyranosyl)oxy]alkanic acid and alkenic acid methyl ester in the form of a brown paste and coexisting polypropylene glucose. This mixture was purified by column chromatography on silica gel to obtain a pure [(2'-O-β-D-glucopyranosyl-β-D-glucopyranosyl)oxy]alkanic acid and alkenic acid methyl ester.

| IR (cm$^{-1}$) | 1740 ($>$C=O ester) | |
|---|---|---|
| NMR [δ(pyridine)]: | 1380-3200 (—OH sugar) | |
| | 900-750 (glucopyranose ring) | |
| | 1.1-1.6 (—CH$_2$—CH$_2$—) | |
| | 3.6 (—O—CH$_3$) | |
| | 3.5-5.0 (sugar) | |
| | 5.5 (—CH=CH— unsaturated fatty acid) | |
| Oil Characterization Analysis: | Acid value | 0 |
| | Hydroxy value | 615 |
| | Saponification value | 88 |
| | Ester value | 87 |

(iv) 100 g of the thus obtained mixture of the [(2'-O-β-D-glucopyranosyl-β-D-glucopyranosyl)oxy]alkanic acid and alkenic acid methyl ester and coexisting polypropylene glycol was placed in an autoclave, together with 0.25 g of potassium hydroxide. Propylene oxide gas was bubbled into the mixture in an amount corresponding to a given addition mole number of propylene oxide, and the mixture was reacted at 100° to 120° C. for 6 hours. After the completion of the reaction, the mixture was neutralized with phosphoric acid and filtered under high pressure to obtain a crude product in the form of a brown paste. This product was purified by column chromatography on silica gel to obtain a pure polyoxypropylene[(2'-O-β-D-glucopyranosyl-β-D-glucopyranosyl)oxy]alkanic acid and alkenic acid methyl ester as a pale yellow paste.

EXAMPLE 1

POSL to be used in the invention and comparative compounds were applied to the skin, and the resistant properties of these oil substances to keratolysis were examined by the Scrub method (Note 1). The results obtained are shown in Table 1.

TABLE 1

| Test compounds | | | | | | Corneocyte counts (number/cm$^2$) | | |
|---|---|---|---|---|---|---|---|---|
| | | $R^1$ | $R^2$ | $R^3$ | a-h | 1st | 2nd | 3rd |
| Present compounds | POSL | CH$_3$ | C$_{15}$H$_{30}$ | CH$_3$ | 12 | 1.6 × 10$^3$ | 7.1 × 10$^3$ | 1.5 × 10$^4$ |
| | POSL | CH$_3$ | C$_{11}$H$_{22}$ | CH$_3$ | 7 | 1.2 × 10$^3$ | 1.0 × 10$^3$ | 1.8 × 10$^3$ |
| | POSL | H | C$_{16}$H$_{30}$ | C$_{12}$H$_{25}$ | 15 | 1.3 × 10$^3$ | 1.4 × 10$^3$ | 1.2 × 10$^4$ |
| | POSL | CH$_3$ | C$_{15}$H$_{28}$ | —(A)$_h$H | 30 | 1.1 × 10$^3$ | 1.1 × 10$^3$ | 1.3 × 10$^3$ |
| Comparative compounds | Vaseline | | | | | 1.6 × 10$^3$ | 1.8 × 10$^3$ | 1.1 × 10$^3$ |
| | Liquid paraffin | | | | | 2.3 × 10$^3$ | 1.9 × 10$^3$ | 1.0 × 10$^3$ |
| | Lanolin | | | | | 1.9 × 10$^3$ | 1.7 × 10$^3$ | 1.6 × 10$^3$ |
| Control | Water | | | | | 8.5 × 10$^4$ | 1.1 × 10$^4$ | 3.2 × 10$^3$ |

(Note 1) Scrub method: Each oil substance was applied to the anterbrachial part of a subject of health in an amount of 0.1 g/4 cm×4 cm, and fixed thereon was a glass cup having a diameter of 2.5 cm. In the glass cup was placed 2 ml of a 0.1 % polyoxyethylene sorbitan monolaurate solution, and the skin was scrubbed with a rod for 60 seconds. Thereafter, each test solution was dyed with Crystal Violet/Fuchsine Base, and the number of corneocyte exfoliated from the skin was counted which was regarded as being a first Scrub number. Second and third Scrub numbers were counted by repeating the same procedure.

From the above results, it can be seen that POSL possesses a skin-protecting ability to the same extent as do the usual oils of the known skin-protecting creams.

EXAMPLE 2

POSL and comparative compounds were examined in their obwashed properties by the following method (Note 2). The results obtained are shown in Table 2.

TABLE 2

| Test compounds | | | | | | Obwashed property (%) |
|---|---|---|---|---|---|---|
| | | $R^1$ | $R^2$ | $R^3$ | a-h | |
| Present compounds | POSL | CH$_3$ | C$_{15}$H$_{30}$ | CH$_3$ | 12 | 96.4 |
| | POSL | CH$_3$ | C$_{11}$H$_{22}$ | CH$_3$ | 7 | 98.2 |
| | POSL | H | C$_{16}$H$_{30}$ | C$_{12}$H$_{30}$ | 15 | 95.5 |
| | POSL | CH$_3$ | C$_{15}$H$_{28}$ | —(A)$_h$H | 30 | 82.5 |
| Comparative compounds | Vaseline | | | | | 17.5 |
| | Liquid paraffin | | | | | 34.2 |
| | Lanolin | | | | | 21.3 |

(Note 2) Obwashed property: 120±2 mg of each test compound was coated homogeneously on a glass plate of 2.5 cm × 3.5 cm with the use of chloroform. The plate was immersed in 2 l of a 0.5% sodium lauryl sulfate aqueous solution having a temperature of 30° C. In this solution was placed a propeller having a diameter of 5 cm, and the solution was stirred at 300 rpm for 2 minutes. Thereafter, the glass plate was transferred to 2 l of water having a temperature of 30° C., and the water was stirred using that propeller at 300 rpm for 1 minute. The plate was rinsed and dried. The weight of the glass plate was measured, and the variance in weight was calculated. The obwashed property was calculated according to the following equation.

$$\text{Obwashed property (\%)} = \left(1 - \frac{\text{Weight of oil residual on glass plate after washing}}{\text{Weight of oil adherent to glass plate before washing}}\right) \times 100$$

From the above results, it can be seen that POSL possesses an extremely high obwashed property as compared with the usual oil substances and can be easily removed by washing.

EXAMPLE 3

Various creams were produced which had the formulation indicated below. The application feeling of each of these sample creams was compared and scored by a panel of ten experts. The results obtained are shown in Table 3.

| Cream Formulation | |
|---|---|
| Test compound | 5 (%) |
| Liquid paraffin | 10 |
| Bees wax | 3 |
| Cetanol | 2 |

-continued

| Cream Formulation | |
|---|---|
| Stearic acid monoglyceride | 3 |
| Polyoxyethylene sorbitan monostearate | 2 |
| Methylparaben | 0.1 |
| Butylparaben | 0.1 |
| Purified water | balance |
| | (% by weight) |

TABLE 3

| Test compounds | | Stick-iness | Moist-ness | Refresh-ness | Spread-ability | Hard-ness |
|---|---|---|---|---|---|---|
| Present compound | POSL $R^1 = CH_3$ $R^2 = C_{15}H_{28}$ $R^3 = CH_3$ a–h = 12 | −0.3 | +1.7 | +0.1 | +0.1 | 0 |
| Comparative compounds | Vaseline | +1.8 | −0.8 | −1.3 | +0.7 | −0.2 |
| | Lanolin | +1.3 | +0.2 | −1.5 | +0.3 | −0.1 |

Note:
Every item in Table 3 was adjudged according to the following evaluation standards. The figures in Table 3 are expresses as the average values of the ten experts' scores.
Severe +2
Fairly +1
Moderate 0
Lacking −1
Nothing −2

From the above results, it can be seen that the cream comprising POSL gives a less sticky and more moist feeling, without any adverse effects being exerted on the other properties, in comparison with the creams composed of the usual oil substances.

EXAMPLE 4

| Hand Cream | |
|---|---|
| (Materials) | |
| (1) POSL ($R^1 = CH_3$, $R^2 = C_{15}H_{28}$ $R^3 = CH_3$, a–h = 12) | 1.5 (%) |
| (2) Stearic acid | 10.0 |
| (3) Stearic acid monoglyceride | 1.5 |
| (4) Polyoxyethylene monostearate | 1.5 |
| (5) Triethanolamine | 0.3 |
| (6) Methylparaben | 0.1 |
| (7) Butylparaben | 0.1 |
| (8) Perfume | 0.2 |
| (9) Purified water | balance |
| | (% by weight) |

(Process)

(1) to (4) were mixed at 70° C., and to this was added with stirring a mixture of (5) to (7) and (9) which had been heated at 70° C. The resulting mixture was emulsified. After the completion of the emulsification, the mixture was allowed to cool to about 40° C., to which was then added (8) to produce a hand cream.

EXAMPLE 5

| Cold Cream | |
|---|---|
| (Materials) | |
| (1) POSL ($R^1 = CH_3$, $R^2 = C_{11}H_{22}$, $R^3 = C_{12}H_{25}$, a–h = 10) | 5.0 (%) |
| (2) Squalane | 5.0 |
| (3) Liquid paraffin | 10.0 |
| (4) Bees wax | 3.0 |
| (5) Lanolin | 1.5 (%) |
| (6) Polyoxyethylene sorbitan monooleate | 3.0 |
| (7) Sorbitan monooleate | 2.0 |
| (8) Methylparaben | 0.1 |
| (9) Butylparaben | 0.1 |
| (10) Perfume | 0.2 |

-continued

| Cold Cream | |
|---|---|
| (Materials) | |
| (11) Purified water | balance |
| | (% by weight) |

(Process)

(1) to (7) and (9) were mixed at 70° C., and to this was added with stirring a mixture of (8) and (11) which had been heated at 70° C. The resulting mixture was emulsified. After the completion of the emulsification, the mixture was allowed to cool to about 40° C., to which was added (8) to produce a cold cream.

EXAMPLE 6

| Cleansing Milk (Milky Lotion) | |
|---|---|
| (Materials) | |
| (1) POSL ($R^1 = CH_3$, $R^2 = C_{11}H_{22}$, $R^3 = CH_3$, a–h = 30) | 1.5 (%) |
| (2) Liquid paraffin | 1.5 |
| (3) Spermaceti | 0.5 |
| (4) Cetanol | 0.5 |
| (5) Sorbitan monostearate | 1.0 |
| (6) Polyoxyethylene monooleate | 0.5 |
| (7) Methylparaben | 0.1 |
| (8) Butylparaben | 0.1 |
| (9) Perfume | 0.1 |
| (10) Purified water | balance |
| | (% by weight) |

(Process)

(1) to (6) and (8) were mixed at 70° C., and to this was added with stirring a mixture of (7) and (10) which had been heated at 70° C. The resulting mixture was emulsified. After the completion of the emulsification, the mixture was allowed to cool to about 40° C., to which was then added (9) to produce a cleansing milk.

EXAMPLE 7

| Hair Cream Oil | |
|---|---|
| (Materials) | |
| (1) POSL ($R^1 = CH_3$, $R^2 = C_{15}H_{28}$, $R^3 = CH_3$, a–h = 10) | 15.0 (%) |
| (2) Liquid paraffin | 3.0 |
| (3) Olive oil | 5.0 |
| (4) Paraffin wax | 1.0 |
| (5) Castor oil | 0.5 |
| (6) Polyoxyethylene sorbitol tetraoleate | 3.5 |
| (7) Methyparaben | 0.1 |
| (8) Butylparaben | 0.1 |
| (9) Perfume | 0.3 |

| Hair Cream Oil | |
|---|---|
| (Materials) | |
| (10) Purified water | balance |
| | (% by weight) |

(Process)

(1) to (6) and (8) were mixed at 70° C. and to this was added with stirring a mixture of (7) and (10) which had been heated at 70° C. The resulting mixture was emulsified. After the completion of the emulsification, the mixture was allowed to cool to about 40° C., to which was then added (9) to produce a hair cream oil.

EXAMPLE 8

| Skin Lotion | |
|---|---|
| (Materials) | |
| (1) POSL ($R^1$ H,  $R^2 = C_{16}H_{30}$, $R^3 = C_{12}H_{25}$,  a–h = 12) | 1.5 (%) |
| (2) Ethanol | 15.0 |
| (3) Polyoxyethylene cetyl ether | 1.5 |
| (4) Methylparaben | 0.1 |
| (5) Perfume | 0.2 |
| (6) Purified Water | balance |
| | (% by weight) |

(Process)

(1) to (6) were stirred at an ordinary temperature to make a homogeneous mixture.

EXAMPLE 9

| Facial Pack | |
|---|---|
| (Materials) | |
| (1) POSL ($R^1 = CH_3$,  $R^2 = C_{13}H_{26}$, $R^3 = -(A)_hH$,  a–h = 5) | 1.5 (%) |
| (2) Polyvinyl alcohol | 15.0 |
| (3) Titanium oxide | 2.0 |
| (4) Ethylene glycol | 4.0 |
| (5) Methylparaben | 0.1 |
| (6) Perfume | 0.2 |
| (7) Purified water | balance |
| | (% by weight) |

(Process)

(7) was heated to 90° C., and to this was added with stirring (2) in limited amounts to make a homogeneous mixture and then added (1), (3), (4) and (5), and the mixture was stirred to become homogeneous and allowed to cool to about 40° C., to which was homogeneously added (6). The mixture was cooled to obtain a facial pack.

EXAMPLE 10

| Foundation Cream | |
|---|---|
| (Materials) | |
| (1) POSL ($R^1 = CH_3$,  $R^2 = C_{15}H_{28}$, $R^3 = CH_3$,  a–h = 10) | 3.0 (%) |
| (2) Isopropyl myristate | 3.0 |
| (3) Stearic acid | 5.0 |
| (4) Talc | 12.0 |
| (5) Titanium oxide | 5.0 |
| (6) Red iron oxide | 0.5 |
| (7) Polyoxyethylene stearate | 2.5 |
| (8) Stearic acid monoglyceride | 1.5 |
| (9) Methylparaben | 0.1 |
| (10) Propylparaben | 0.1 |
| (11) Perfume | 0.2 |
| (12) Purified water | balance |
| | (% by weight) |

(Process)

(1) to (3), (7), (8) and (10) were mixed at 70° C., and to this was added with stirring a mixture of (9) and (12) which had been heated at 70° C. To the resulting mixture were added with stirring (4) to (6) while keeping the temperature at 70° C. The mixture was allowed to cool to a temperature less than about 40° C., to which was then added (11) to produce a foundation cream.

What we claim is:

1. A skin protecting cosmetic composition in emulsion or solution form of from 0.1 to 100% of a hydroxypropyl-etherified glycolipid ester represented by the formula:

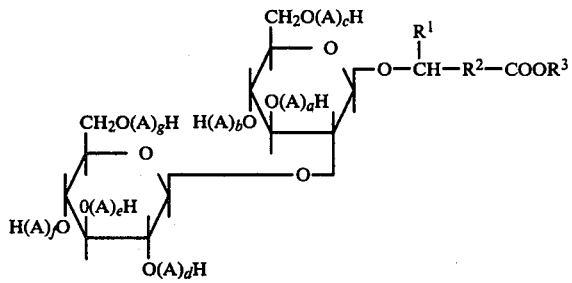

wherein $R^1$ represents methyl or hydrogen; $R^2$ represents a saturated or unsaturated hydrocarbon group having carbon atoms of 11 to 15 when $R^1$ is methyl, or a saturated or unsaturated hydrocarbon group having carbon atoms of 12 to 16 when $R^1$ is a hydrogen atom; A represents the Group

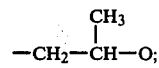

$R^3$ represents a saturated or unsaturated hydrocarbon group having carbon atoms of 1 to 20 or $-(A)_hH$; and a, b, c, e, d, f, g and h are each integers, whose sum ranges from 1 to 60, as the oil component, in an aqueous vehicle.

2. A skin-protecting cosmetic composition according to claim 1, wherein said hydroxypropyl-etherified glycolipid ester is contained in an amount of 5 percent by weight of the composition.

3. A skin-protecting cosmetic composition according to claim 1, wherein said hydroxypropyl-etherified glycolipid ester is contained in an amount of 1.5 percent by weight of the composition.

* * * * *